United States Patent [19]
Coffman

[11] Patent Number: 5,510,393
[45] Date of Patent: Apr. 23, 1996

[54] METHOD FOR PRODUCING METHANOL

[75] Inventor: John A. Coffman, Ballston Spa, N.Y.

[73] Assignee: Wright Malta Corporation, Ballston Spa, N.Y.

[21] Appl. No.: 460,057

[22] Filed: Jun. 2, 1995

Related U.S. Application Data

[63] Continuation of Ser. No. 349,912, Dec. 6, 1994.

[51] Int. Cl.$^6$ ................................................. C07C 27/06
[52] U.S. Cl. .......................................... 518/703; 518/700
[58] Field of Search .................................. 518/703, 700; 422/197, 201

[56] References Cited

U.S. PATENT DOCUMENTS

| | | | |
|---|---|---|---|
| 4,084,379 | 4/1978 | Schwartzman | 60/611 |
| 4,326,041 | 4/1982 | Bahnizch | 518/703 |
| 4,339,413 | 7/1982 | Lahne et al. | 60/641 |
| 4,374,288 | 2/1983 | Scragg | 422/200 |
| 4,559,207 | 12/1985 | Hiller et al. | 422/197 |
| 4,597,772 | 7/1986 | Coffman | 48/11.1 |
| 4,650,814 | 3/1987 | Keller | 518/703 |
| 5,254,781 | 10/1993 | Calamur et al. | 585/500 |
| 5,266,281 | 11/1993 | Kao et al. | 422/197 |
| 5,362,453 | 11/1994 | Marsch | 422/197 |

FOREIGN PATENT DOCUMENTS 197811  11/1978  Germany .
117336  4/1992  Japan .

OTHER PUBLICATIONS

"Improved Methanol Process" by Emil Supp. *Hydrocarbon Processing*, Mar. 1981. pp. 71–75.

*Primary Examiner*—Werren B. Lone
*Attorney, Agent, or Firm*—Ratner & Prestia

[57] ABSTRACT

A graded temperature methanol reactor includes an inclined container containing a liquid heat transfer medium, such as water, having a varying temperature along the container. Conduits, extending through the container and in contact with heat transfer medium, conduct a feed gas having hydrogen and carbon monoxide and permit heat transfer between the feed gas and the heat transfer medium. A copper catalyst is disposed within each conduit to cause the hydrogen and carbon monoxide to react to form methanol, which condenses as the temperature decreases along the container from the upper end to the lower end. Preferably, the conduits are configured as a rotor and can be rotated relative to the container. By using this methanol reactor, methanol can be produced from a feed gas having hydrogen and carbon monoxide in a 2:1 molecular ratio, regardless of the source of this feed gas. For example, this feed gas can be produced by a biomass gasification and reforming process, and the methanol reactor can be interrelated with the gasification process.

14 Claims, 3 Drawing Sheets

METHOD FOR PRODUCING METHANOL

This application is a division of application Ser. No. 08/349,912, filed Dec. 6, 1994, (status: pending).

FIELD OF THE INVENTION

This invention relates to a reactor and process for producing methanol from a feed gas having hydrogen and carbon monoxide in an approximate 2:1 molecular ratio. In addition, the present invention is directed to a process for producing methanol from a feed of a biomass containing carbon, hydrogen and oxygen.

BACKGROUND OF THE INVENTION

Methanol synthesis is the simple addition of hydrogen to carbon monoxide. This reaction is reversible, with the position of equilibrium determined by pressure, temperature, and concentration as follows:

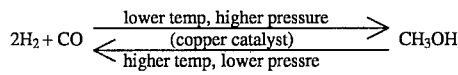

The reaction rate of approach to equilibrium is a function of temperature alone. More particularly, as temperature increases, the reaction rate increases.

Two known commercial processes for producing methanol use uniform temperature reactors. In the first known process, hydrogen and carbon monoxide are fed to a reactor having an "optimum" temperature. An optimum temperature is sufficiently low to drive the above methanol synthesis reaction towards methanol without significantly compromising the rate of reaction. Then, the reactor is quenched in order to condense the methanol so that it can then be separated. After methanol separation, the reactor is again heated up for the next cycle.

The second known uniform-temperature methanol reactor involves passing the reactants through a boiling water reactor. Then, the exit gas from the reactor is fed to a condenser where the methanol can be separated. Subsequently, the gas is rewarmed and recycled, with the addition of fresh synthesis gas to prevent the buildup of impurities.

In each of these two known processes, the reaction is driven gradually towards completion, with only about a ten to twenty percent degree of reaction with each stage. In addition, each process requires the step of purging a certain amount of the stripped gas during each cycle, in order to prevent a significant build-up of methane and trace inerts, such as nitrogen.

SUMMARY OF THE INVENTION

The present invention relates to a graded temperature methanol reactor, which includes an inclined container containing a liquid heat transfer medium, such as water, having a varying temperature along the length of the container. The container has an inlet opening near its lower end to permit the heat transfer medium to enter the container, and an outlet opening near its upper end to permit the heated heat transfer medium to exit the container as a vapor. The reactor also includes conduits extending within the container and in contact with the heat transfer medium. The conduits conduct a feed gas having hydrogen and carbon monoxide in an approximate 2:1 molecular ratio and permit heat transfer between the feed gas and the heat transfer medium. A copper catalyst is disposed within each conduit to cause the hydrogen and carbon monoxide to react to form methanol, which condenses as the temperature decreases along the container from the upper end to the lower end.

According to another embodiment of the present invention, the conduits are configured as a rotor which is disposed coaxially within the container. According to this embodiment of the present invention, a device, such as a drive motor along with a drive gear, rotates the rotor relative to the container. Also, the rotor includes a first bored stub shaft extending through the top end plate of the container to define an intake bore for conducting feed gas to the conduits. The rotor includes a second bored stub shaft extending through the bottom end plate of the container.

The present invention also includes a process for producing methanol from a feed gas having hydrogen and carbon monoxide in an approximate 2:1 molecular ratio. The process includes first compressing and heating the feed gas, preferably to a pressure of about 1,400 psi to 1600 psi and to a temperature of about 550° F. to 650° F. After a heat transfer medium is introduced the interior of an inclined vessel, the feed gas is introduced into the conduits extending through the interior of the vessel. The feed gas is exposed to a copper catalyst which is disposed in the conduits to cause the hydrogen and carbon monoxide to react to form methanol which condenses along the vessel causing further formation of methanol. According to another embodiment of the process of the present invention, the process includes rotating the conduits within the vessel.

The present invention also includes a process for producing methanol from biomass. The process according to this embodiment includes adding water and an alkaline catalyst to the biomass feed to form a feed mixture, which is charged into an interior chamber of an inclined rotor kiln. The feed mixture is heated to a temperature of from about 1050° F. to 1150° F. to produce a first gas mixture including hydrogen and carbon monoxide. After traveling through the chamber of the rotor kiln, the gas mixture is heated in a gas reformer while being exposed to a nickel catalyst to form a reformed gas mixture having a hydrogen and carbon monoxide in an approximate 2:1 molecular ratio. Then, the reformed gas mixture is conducted through pipes which extend along the rotor kiln through its interior chamber. After condensing the mixture, impurities are removed and then the mixture is compressed and heated to about 1400 psi to 1600 psi and a temperature of from about 550° F. and 650° F. Then, this feed gas is introduced into the conduits extending through the interior of the methanol reactor according to the present invention.

It is to be understood that both the foregoing general description and the following detailed description are exemplary, but not restrictive, of the invention.

BRIEF DESCRIPTION OF THE DRAWINGS

The invention is best understood from the following detailed description when read in connection with the accompanying drawings, in which.

DETAILED DESCRIPTION OF THE INVENTION

Figure 1:
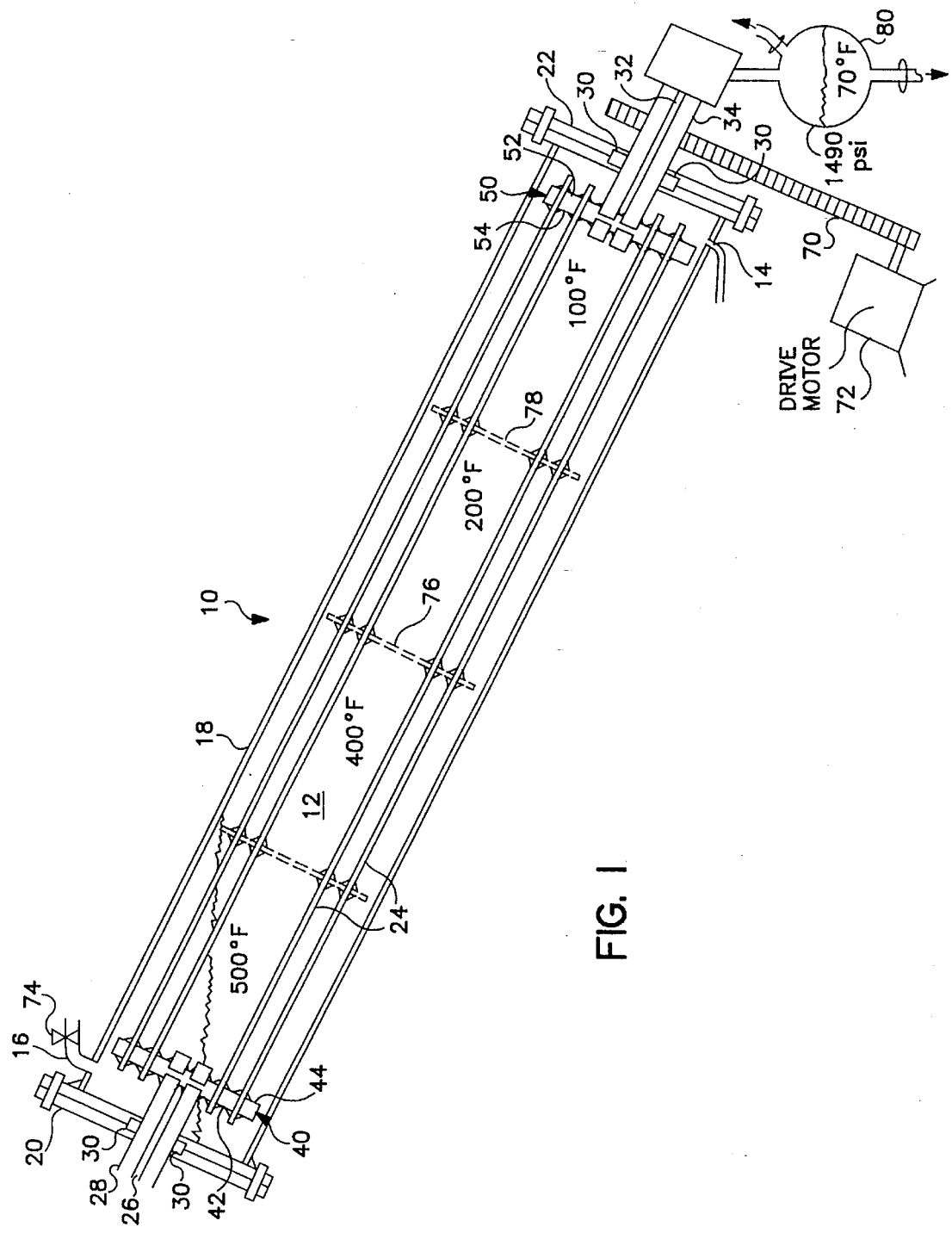
FIG. 1 is a partial longitudinal view of a methanol reactor according to the present invention.

FIG. 1 shows an inclined container 10 which is configured as a cylindrical pressure vessel. Container 10 contains a liquid heat transfer medium 12, such as water, which has a varying temperature along the length of the container. More particularly, the liquid heat transfer medium 12 is introduced into container 10 through inlet opening 14 as a cooled liquid. The heat transfer medium exits container 10 as a vapor through an outlet conduit 16 (defining an outlet opening) near the upper end of the container.

Disposed within outlet conduit 16 is a valve 74, which is configured to place the heat transfer medium under pressure such that most of the heat transfer medium exists as a liquid in the container 10. For example, if the gas entering the container 10 has a temperature of about 600° F., and water is used as the heat transfer medium, valve 74 would be configured to keep the pressure of the heat transfer medium in the container 10 at about 700 psi.

According to one embodiment of the invention, the liquid heat transfer medium is water and is introduced through inlet opening 14 at a temperature of about 100° F. and exits outlet conduit 16 as a vapor at a temperature of about 550° F. The temperature of the water gradually increases from the lower end to the upper end of container 10. As the temperature of the water increases, it becomes less dense so that it progresses toward the upper end of container 10. Any other suitable heat transfer medium may be used, so long as the heat transfer medium becomes less dense with increased temperature.

Container 10 includes an outer cylindrical surface 18, a top end plate 20 at the upper end of container 10 and a bottom end plate 22 at the lower end of container 10. As shown in FIG. 1, container 10 is inclined slightly. According to one embodiment of the invention, the reactor is disposed at an angle of about 15° from horizontal, although the angle of inclination can vary significantly depending on process conditions.

As shown in FIG. 1, a plurality of conduits are disposed within container 10 and are in contact with heat transfer medium 12. Conduits 24 conduct a feed gas having hydrogen and carbon monoxide in an approximate 2:1 molecular ratio along their length from the upper end to the lower end of container 10. In addition, conduits 24 permit heat transfer between the feed gas and the heat transfer medium.

Each of the conduits 24 (or pipes) are in fluid communication with an intake bore 26 defined by a first bored stub shaft 28 which extends through top end plate 20. Seals 30, such as known stuffing boxes, are disposed between first bored stub shaft 28 and top end plate 20. Each of the conduits 24 are also in fluid communication with an exhaust bore 32 defined by a second bored stub shaft 34 which extends through bottom end plate 22. Once again, seals 30, such as stuffing boxes, are disposed between second bored stub shaft 34 and bottom end plate 22.

Figure 2:
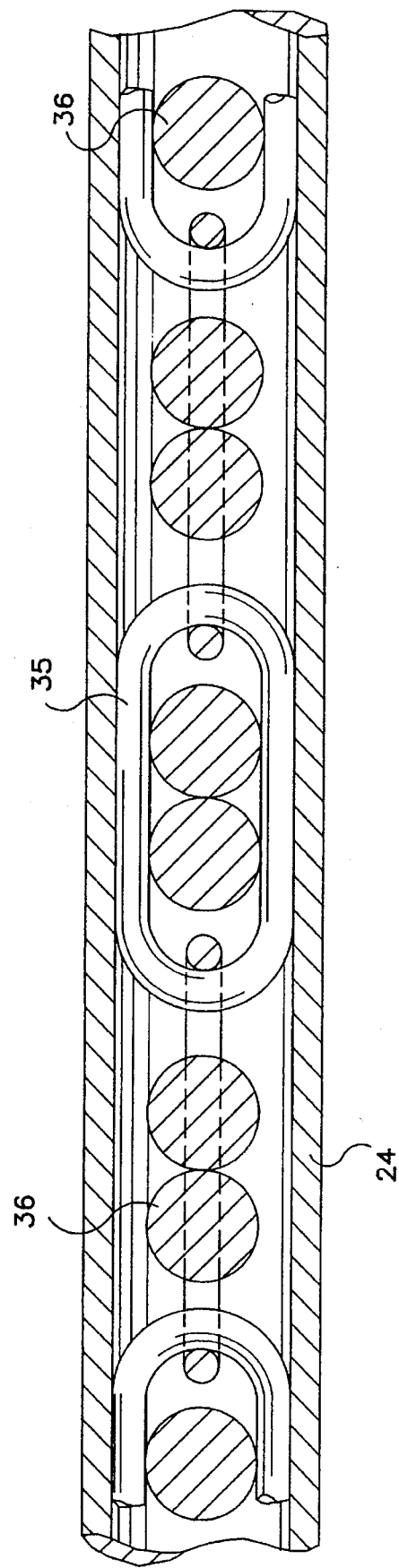
FIG. 2 is an enlarged longitudinal view of a conduit of the methanol reactor shown in FIG. 1.

A copper catalyst is disposed within each of the conduits 24. The copper catalyst, which causes the hydrogen and carbon monoxide to react to form methanol, may be disposed within conduits 24 in any known manner, such as by adhering the copper catalyst to the inside of conduits 24, or by placing the copper catalyst within a screen disposed within each conduit 24. Alternatively, as shown in FIG. 2 which is an enlarged view of a conduit 24, a chain 35 may be disposed within each conduit 24 and the copper catalyst may be disposed as pellets 36 within the links of the chain 35.

As shown in FIG. 1, a double-plate intake manifold 40 is disposed between first bored stub shaft 28 and conduits 24. Intake manifold 40 includes a first plate 42 closer to the upper end and having a second plate 44 closer to the bottom end and spaced from first plate 42 to form an intake manifold interior. Each plate 42, 44 includes a plurality of holes through which the conduits individually extend.

Similarly, a double-plate exhaust manifold 50 includes a first plate 52 closer to the lower end of container 10 and a second plate 54 closer to the upper end of container 10 and spaced from first plate 52 to form an exhaust manifold interior. Each plate 52, 54 has a plurality of holes through which conduits 24 individually extend. Conduits 24 have bores near their ends to permit communication between the interior of conduits 24 and the intake manifold interior, and the interior of conduits 24 and the exhaust manifold interior. The intake and exhaust manifold are similar to that shown in FIG. 5 of applicant's co-pending application entitled APPARATUS FOR PRODUCING METHANE-RICH GAS USING A FIXED KILN WITH ROTOR STEAM GASIFIER, filed on the same day as this application and incorporated herein by reference.

Covers individually engage each of the conduits 24 at the ends of the conduits. In addition, swivel connections may be individually mounted to the covers and individually connect the chains to the covers for permitting relative rotation between the chains and the covers as the conduits 24 rotate.

According to an embodiment of the present invention, the conduits 24 are configured as a rotor. According to this embodiment, a drive gear 70 is driven by a motor 72. Gear 70 is coupled to either first bored stub shaft 28 or second bored stub shaft 34 and causes the stub shaft to rotate. Because the conduits 24 are connected to the stub shafts, the conduits also rotate along with the stub shaft. Thus, conduits 24 are disposed as a rotor coaxially with container 10.

According to this embodiment, the catalyst is preferably selected as pellets 36 and chains are used to maintain the catalyst pellets 36 in position. Accordingly, when the conduits 24 rotate, the copper catalyst pellets 36 are slightly abraded by being contacted against the chain links and the interior of the conduits 24. This causes the copper catalyst to stay fresh longer. Another advantage of configuring the conduits 24 as a rotor is improved heat transfer. Movement of the conduits 24 through the water (e.g., at about 1–2 rpm) will aid heat transfer from the conduits 24 to the heat transfer medium. Also, the chains and pellets will cause gentle gas turbulence within the pipes, and their movement with rotation will aid in the heat transfer from gas to the conduits 24.

Also, the reactor may include at least one spider plate 76 which is mounted to the exterior of the conduits 24. The spider plates 76 serve to stabilize conduits 24. Also, the spider plates 76 have bores 78 for permitting flow of the heat transfer medium.

The system also includes a separating vessel 80, which is in fluid communication with exhaust bore 32. The separating vessel serves to separate liquid methanol from the purge gas.

The process according to the present invention includes compressing and heating a feed gas having hydrogen and carbon monoxide in an approximate 2:1 molecular ratio. Preferably, the feed gas is compressed until a pressure of 1400 psi to 1600 psi is achieved and is heated until the temperature of the feed gas is from about 550° F. to 650° F. Even more preferably, the feed gas is compressed until a pressure of 1500 psi is achieved and is heated until a temperature of 600° F. is achieved. The feed gas is then introduced into the plurality of conduits 24 through intake bore 26 of first bored stub shaft 28. The heat of the gas is transferred to the heat transfer medium in the interior of container 10.

Upon exposure to a copper catalyst, hydrogen and carbon monoxide react to form methanol in each conduit 24. As the reacting gases travel downward through conduits 24, the temperature decreases gradually which causes further formation of methanol from hydrogen and carbon monoxide. Then, at a low enough temperature, for example of about 400° F. at 1495 psi, the methanol begins to condense which drives the equilibrium reaction of methanol further to the right in the gaseous phase due to the decrease in methanol concentration in the gaseous phase. This reaction is continued until the temperature of the gas drops to a range of from about 70° F. to 130° F., and preferably about 100° F. With this process, a reaction yield of approximately 70% is attained.

The process may also include placing a chain 35 in each of the plurality of conduits and placing copper catalysts as pellets 36 in the links of the chains thereby exposing the gas to the copper catalyst pellets 36 as the gas is conducted through the conduits 24. In addition, the process may include separating unreacted feed gas from the methanol product. Furthermore, the process may include filtering the methanol product to remove particulates formed by catalyst shedding. The process may also include rotating the conduits, preferably at a speed of about 1 to 2 rpm.

Figure 3:
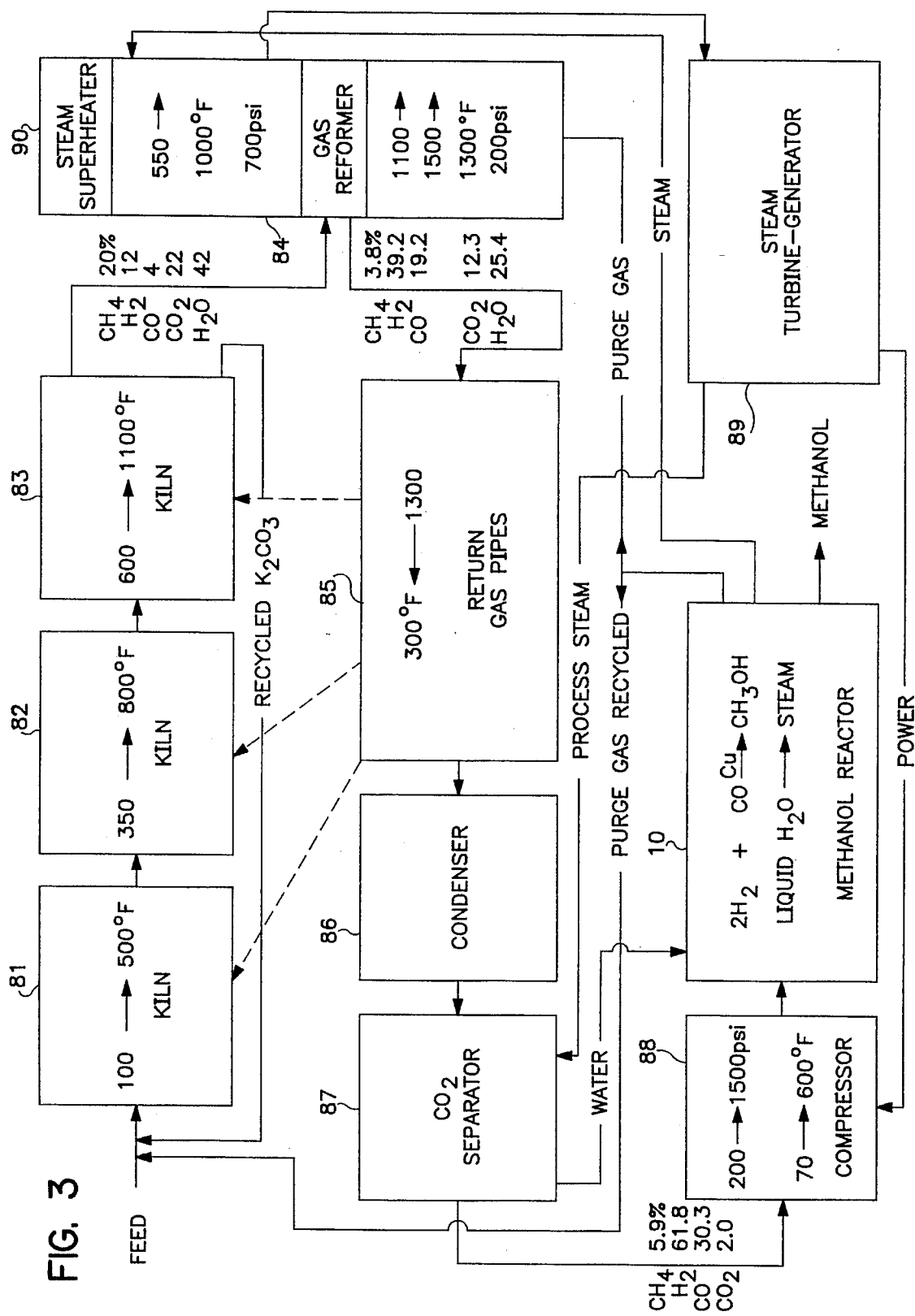
FIG. 3 is a schematic diagram showing a process for producing methanol according to the present invention.

The process of the present invention also includes a process for producing methanol from a biomass feed containing carbon, hydrogen and oxygen. According to this process, the biomass feed is first gasified by using a fixed kiln with rotor steam gasifier as disclosed in U.S. Pat. No. 4,597,772, which is incorporated herein by reference, or by the gasifier disclosed in applicant's co-pending application entitled APPARATUS FOR PRODUCING METHANE-RICH GAS USING A FIXED KILN WITH ROTOR STEAM GASIFIER, filed on the same day as this application and also incorporated herein by reference. The gas produced by the gasifier process of either of these references is reformed, gives its heat to the gasification process, is purified, compressed and heated, then fed to a methanol reactor according to the present invention. FIG. 3 shows a block diagram of the interrelation between the gasifier process of one of the two references and the methanol reactor of the present invention.

The first step of the process is to add water and an alkaline catalyst, such as potassium carbonate or sodium carbonate, to the biomass feed to form a feed mixture. The term biomass is defined in the '772 patent, and might include wood chips or corn stalks and about fifty percent water. Stages 81 through 83 of FIG. 3 represent the standard stages of the gasification process as the feed travels through the body of the kiln. During stage 81, moisture is evaporated as the temperature increases from 100° F. to 500° F. During stage 82, the reactants are pyrolyzed into gas, liquids, and char, as the temperature increases from 350° F. to 800° F. Finally, in stage 83, char and liquids are gasified by steam as the temperature increases to 1100° F. As shown in the '772 patent, the rotor kiln is tilted to permit gravity-driven travel in a first direction and includes a plurality of pipes extending along the rotor kiln, wherein each of the pipes defines a pipe flowpath isolated from the interior chamber of the kiln. During stages 81 through 83, the feed mixture is gradually heated to a temperature of about 1050° F. to 1150° F. to produce a gas mixture including $CH_4$, $H_2$, $CO$, $CO_2$, $H_2O$, a trace amount of $H_2S$, and about 1–2% condensable organic compounds.

The gas flows from the gasifier to a reformer 84, where it is heated in the presence of a nickel catalyst from 1100° to 1500° F. The small amount of liquid and tar in the gas as it enters the reformer cracks along with the methane. Traces of $H_2S$ similarly are not harmful; nickel is not easily poisoned at these high temperatures in the presence of steam (based on an equilibrium analysis). The reformer 84 causes the molar gas composition to change as follows:

|         | 1100° F. | 1500° F. |
|---------|----------|----------|
| $CH_4$  | 20%      | 3.8%     |
| $H_2$   | 12       | 39.2     |
| $CO$    | 4        | 19.2     |
| $CO_2$  | 22       | 12.3     |
| $H_2O$  | 42       | 25.4     |

Most of the methane has been steam-reformed to $H_2$ and $CO$, and some of the $CO_2$ has been reduced to $CO$. Also, the ratio between $H_2$ and $CO$ is now 2.04 to 1.00, just right for methanol synthesis. This gas composition shift is strongly endothermic, and the heat of reaction is supplied by burning part of the purge gas from the methanol reactor, as shown in FIG. 3.

The hot reformed gas gives a little of its heat to the incoming gas, and then flows from the reformer 84 into the returning gas pipes 85 of the gasifier, with significantly more enthalpy than when it emerged from the kiln. The reformed gas will easily support the gasification process in regenerative mode. There are chains and pellets in the gas pipes, but unlike the usual gasification system, the pellets are inert ceramic, placed in the pipes just for turbulence and heat transfer, and the gas does not change in composition in its passage from the hot to the cool end of the kiln.

As the temperature decreases in the returning gas pipes from 1300° F. to 300° F., some of the steam will condense in the pipes near the cool end, and give its head of condensation to the warming of the incoming feedstock within the kiln. A condenser 86 completes the condensation as the temperature is decreased to 70° F. Then, the gas is stripped of traces of $H_2S$ and all but about two percent of $CO_2$ (needed to keep the methanol catalyst at the right degree of oxidation) in a known $CO_2$ separator. For example, $CO_2$ separator 87 might represent a $CO_2$ absorption vessel and a $CO_2$ release vessel which makes use of the Benfield process, which employs the following reversible reaction:

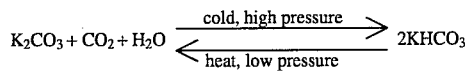

At this point, the molar gas composition of the gas is approximately as follows: 5.9% $CH_4$, 61.8% $H_2$, 30.3% $CO$, and 2.0% $CO_2$. Then, the gas is compressed adiabatically in a compressor 88 and fed into the methanol reactor.

As mentioned above, a quantity of the unreacted feed gas (i.e, purge gas) is conducted to the gas reformer 84 where it is burned for heating the gas fed to the gas reformer 84 from the kiln. The quantity of purge gas delivered to the gas reformer 84 should be sufficient for heating the gas mixture to about 1500° F. The remaining purge gas is recycled to the interior chamber of the rotor kiln through the biomass feed system.

According to a preferred embodiment of the invention, steam from the methanol reactor, which is formed by the transfer of heat from the feed gas, is conducted to a steam superheater 90 atop the gas reformer to form superheated steam. This superheated steam may then be conducted to a steam turbine-generator 89 for generating power. The steam which has imparted some of its energy to the steam turbine-generator 89 may then be conducted to the $CO_2$ separator 87 for transferring its heat of condensation to form water, which may subsequently be returned to the methanol reactor 10.

Typically, the step of gradually heating the feed mixture as it progresses throughout the kiln, as shown in blocks 81 through 83, lasts for about 30 to 90 minutes. Initially, the feed mixture is heated by an external source of heat, such as by providing steam in returning gas pipes 85. The application of heat from the external source of heat may be discontinued as soon as the total heat given off by the process and transferred to the feed mixture, including the heat given off by the reformed gas mixture in the pipes, is sufficient to heat the feed mixture and the gas mixture in the interior chamber to a temperature of about 1100° F. at the output end of the kiln. The steam in the back-coming gas will condense in the pipes near the cool end of the kiln and give its heat of condensation to the warming of the incoming feedstock within the kiln. The condenser completes the condensation.

The methanol reactor to go with a 300 ton/day gasifier might be 30 ft. long and 4 ft. in diameter, with an array of about 400 1" diameter heavy-walled pipes forming the rotor. It is akin, conceptually, to a fire-tube boiler, with the synthesis gas-to-methanol exotherm providing the heat to raise the steam.

The methanol reactor of the present invention is sturdy and straightforward to build. Most of the components of the reactor can be constructed from plate stock. For example, the spider plates can be simple flat plate, bored for the gas pipes, with smaller holes in the spider plates between the pipes for water flow. The pipes can be spot-welded to the spider plates to give torque and sag resistance to the rotor structure. The manifolds similarly will be constructed from plate stock, with the shafts and pipes projecting through plates of the manifolds. As mentioned above, the pipes are bored between the plates of the manifold for gas entrance and egress and are plugged outside the plates for ease in cleaning. The pipes are welded to the outer surface of the plates of the manifold. The assembly is completed by welding a hoop around the perimeter of the plates.

Although illustrated and described herein with reference to certain specific embodiments, the claims are not intended to be limited to the details shown. Rather, the claims should be read to include various modifications of the details shown without departing from the spirit of the invention.

What is claimed:

1. A process for producing methanol from a feed gas having hydrogen and carbon monoxide in an approximate 2:1 ratio, said process comprising the steps of:
    (a) compressing and heating said feed gas;
    (b) introducing a heat transfer medium into an interior of an inclined vessel;
    (c) introducing the feed gas from step (a) into a plurality of conduits extending through the interior of said vessel, which conduits are in contact with said heat transfer medium and define conduit flow paths isolated from said interior;
    (d) exposing said gas to a copper catalyst disposed in said conduit flow paths to cause the hydrogen and carbon monoxide to react to form methanol, while conducting said gas through said conduit flow paths to cause the temperature of said gas to gradually drop, causing further formation of methanol from the hydrogen and carbon monoxide and causing the methanol to condense to a liquid.

2. A process in accordance with claim 1 wherein:
    step (a) is continued until the pressure of said feed gas is from about 1400 psi to 1600 psi and the temperature of said feed gas is from about 550° F. to 650° F.; and
    step (d) is continued until the temperature of said gas drops to a temperature of from about 70° F. to 130° F.

3. A process in accordance with claim 1 wherein:
    step (a) includes compressing said feed gas to about 1500 psi and heating said feed gas to about 600° F.; and
    step (d) includes permitting the temperature of said gas and liquid methanol mixture to gradually drop to about 100° F.

4. A process in accordance with claim 1 further comprising:
    placing a chain in each of said plurality of conduits;
    placing said copper catalyst as pellets in the links of said chain thereby exposing said gas to said copper catalyst pellets as said gas is conducted through said conduits.

5. A process in accordance with claim 1 further comprising separating unreacted feed gas from the methanol product.

6. A process in accordance with claim 5 further comprising filtering the methanol product to remove particulates formed by catalyst shedding.

7. A process in accordance with claim 1 further comprising rotating said conduits within said vessel.

8. A process in accordance with claim 7 further comprising rotating said conduits at a speed of about 1 to 2 rpm.

9. A process for producing methanol from a feed containing carbon, hydrogen and oxygen, said process comprising the steps of:
    (a) adding water and an alkaline catalyst to the feed to form a feed mixture;
    (b) charging said feed mixture into an interior chamber of a rotor kiln at a first end of said rotor kiln, which is tilted to permit gravity-driven travel in a first direction along said rotor kiln and which has a plurality of pipes extending along said rotor kiln in said first direction, wherein each of said pipes defines a pipe flow path isolated from said interior chamber;
    (c) gradually heating said feed mixture to a temperature of from about 1050° F. to 1150° F. to produce a gas mixture including $CH_4$, $H_2$, CO, $CO_2$, $H_2O$, a trace amount of $H_2S$, and about 1–2% condensable organic compounds;
    (d) heating said gas mixture in a gas reformer while exposing said gas mixture to a nickel catalyst in said gas reformer to form a reformed gas mixture having $H_2$ and CO in an approximate 2:1 ratio;
    (e) conducting said reformed gas mixture to said pipe flow paths at said second end of said rotor kiln and permitting said reformed gas mixture to flow through said pipes back to said first end of said pipes, wherein said reformed gas mixture in said pipes gives off the heat needed in step (c) to said feed mixture and said gas mixture in said interior chamber to cool said reformed gas mixture to a temperature of about 300° F. to become a partially condensed mixture;
    (f) condensing said partially condensed mixture to form a condensed mixture;
    (g) removing impurities including said trace amount of $H_2S$ from said condensed mixture and most of said $CO_2$ in an absorption vessel to form a substantially pure mixture;
    (h) compressing and heating said substantially pure mixture to a pressure of from about 1400 psi to 1600 psi and a temperature of from about 550° F. to 650° F. to form a feed gas having hydrogen and carbon monoxide in an approximate 2:1 ratio;

(i) introducing cool water into an interior of an inclined vessel;

(j) introducing the feed gas into a plurality of conduits extending through the interior of said vessel, which conduits are in contact with said cool water and define conduit flow paths isolated from said interior;

(k) exposing said feed gas to a copper catalyst disposed in said conduit flow paths to cause the hydrogen and carbon monoxide to react to form methanol, while conducting said feed gas through said conduit flow paths to cause the temperature of said feed gas to gradually drop, causing further formation of methanol from the hydrogen and carbon monoxide and causing the methanol to condense to a liquid; and (l) separating unreacted feed gas from the methanol product.

10. A process in accordance with claim 9 further comprising:

conducting a quantity of said unreacted feed gas to said gas reformer and burning said quantity of said unreacted feed gas at said gas reformer, wherein said quantity is sufficient for heating said gas mixture in said gas reformer; and conducting a remaining quantity of said unreacted feed gas to said interior chamber of said rotor kiln at said first end of said rotor kiln.

11. A process in accordance with claim 9 further comprising:

conducting steam from said vessel, formed by the transfer of heat from said feed gas, to a steam superheater atop said gas reformer to form superheated steam;

conducting said superheated steam to a turbine generator to generate power;

conducting the steam from said turbine generator to said absorption vessel for transferring its heat of condensation to form water; and returning the water from said absorption vessel to said vessel.

12. A process in accordance with claim 9, wherein step (c) is continued for about 30 to 90 minutes.

13. A process in accordance with claim 9 wherein step (c) includes initially heating said feed mixture with an external source of heat.

14. A process in accordance with claim 13, wherein step (c) further includes discontinuing the application of heat from said external source of heat as soon as the total heat given off by the process and transferred to said feed mixture, including the heat given off by said reformed gas mixture in said pipes, is sufficient to heat said feed mixture and said gas mixture in said interior chamber to a temperature of about 1100° F. at said second end of said rotor kiln.

* * * * *